US009739707B2

(12) United States Patent
Ogasawara

(10) Patent No.: US 9,739,707 B2
(45) Date of Patent: Aug. 22, 2017

(54) OIL CONCENTRATION MEASUREMENT SYSTEM AND OIL CONCENTRATION MEASUREMENT METHOD

(71) Applicant: ACT FIVE CO., LTD., Kyoto-shi, Kyoto (JP)

(72) Inventor: Kazuhisa Ogasawara, Kyoto (JP)

(73) Assignee: ACT FIVE CO., LTD., Kyoto (JP)

( * ) Notice: Subject to any disclaimer, the term of this patent is extended or adjusted under 35 U.S.C. 154(b) by 0 days.

(21) Appl. No.: 15/314,813

(22) PCT Filed: Jan. 19, 2016

(86) PCT No.: PCT/JP2016/051369
§ 371 (c)(1),
(2) Date: Nov. 29, 2016

(87) PCT Pub. No.: WO2016/132795
PCT Pub. Date: Aug. 25, 2016

(65) Prior Publication Data
US 2017/0199118 A1    Jul. 13, 2017

(30) Foreign Application Priority Data

Feb. 17, 2015 (JP) .................................. 2015-028202

(51) Int. Cl.
*G01N 21/33* (2006.01)
*G01N 33/28* (2006.01)

(52) U.S. Cl.
CPC ......... *G01N 21/33* (2013.01); *G01N 33/2835* (2013.01)

(58) Field of Classification Search
CPC ............. G01N 21/8507; G01N 21/314; G01N 21/3554; G01N 21/3559;
(Continued)

(56) References Cited

U.S. PATENT DOCUMENTS 5,411,558 A * 5/1995 Taniguchi ............... C10L 1/328
 44/301
5,772,606 A 6/1998 Ashibe et al.
(Continued)

FOREIGN PATENT DOCUMENTS

EP 670492 A2 9/1995
JP S56-147042 A 11/1981
(Continued)

OTHER PUBLICATIONS

Apr. 12, 2016 International Search Report issued in International Patent Application No. PCT/JP2016/051369.
(Continued)

*Primary Examiner* — Michael P Stafira
(74) *Attorney, Agent, or Firm* — Oliff PLC

(57) ABSTRACT

An oil concentration measurement system and method measure the concentration of oil over a wide concentration range and is applicable in a continuous measurement of oil concentration. A measurement-target liquid containing a known kind of oil component, absorbance spectrum is measured within a predetermined waveband where absorption of light is observed. If a predetermined criterion is met, a concentration value of the oil component is determined based on absorbance at a predetermined wavelength within the predetermined waveband and also on a first calibration curve showing relationship between the component concentration and absorbance at the predetermined wavelength. If the predetermined criterion is not met, a concentration value is determined based on the wavelength at which the absorbance has a predetermined absorbance value within the absorbance spectrum and also on a second calibration curve showing the relationship between the component concentration and wavelength at which the absorbance has the predetermined absorbance value.

10 Claims, 8 Drawing Sheets

(58) Field of Classification Search
CPC ....... G01N 2021/3129; G01N 21/5907; G01N 21/94; G01N 21/31; G01N 21/3577; G01N 2333/495; G01N 2800/065; G01N 2800/085; G01N 2800/12
See application file for complete search history.

(56) References Cited

U.S. PATENT DOCUMENTS

| | | | |
|---|---|---|---|
| 7,616,316 B1 | 11/2009 | Silver et al. | |
| 8,023,690 B2* | 9/2011 | DiFoggio | G01J 3/02 382/100 |
| 2010/0229623 A1* | 9/2010 | Abad | E21B 49/08 73/1.02 |
| 2013/0277551 A1* | 10/2013 | Bourrel | G01N 33/28 250/282 |

FOREIGN PATENT DOCUMENTS

| | | |
|---|---|---|
| JP | H07-294519 A | 11/1995 |
| JP | H09-61349 A | 3/1997 |
| JP | H09-292328 A | 11/1997 |
| JP | 2011-220941 A | 11/2011 |
| WO | 2004/029592 A1 | 4/2004 |
| WO | 2013/138929 A1 | 9/2013 |

OTHER PUBLICATIONS

Apr. 12, 2016 Written Opinion issued in International Patent Application No. PCT/JP2016/051369.
May 22, 2017 Extended European Search Report issued in European Patent Application No. 16752184.8.

* cited by examiner

Fig. 4
(a) AMOUNT OF LIGHT TRANSMITTED THROUGH SAMPLE CONTAINING MP15
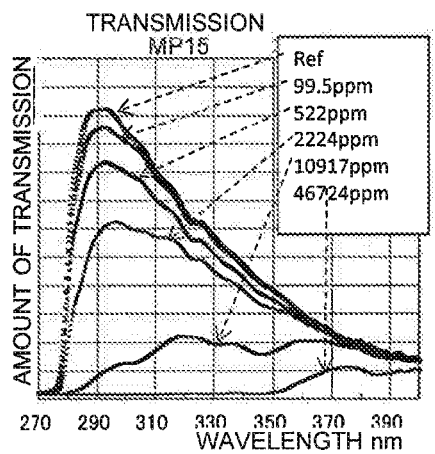
(b) ABSORBANCE OF SAMPLE CONTAINING MP15
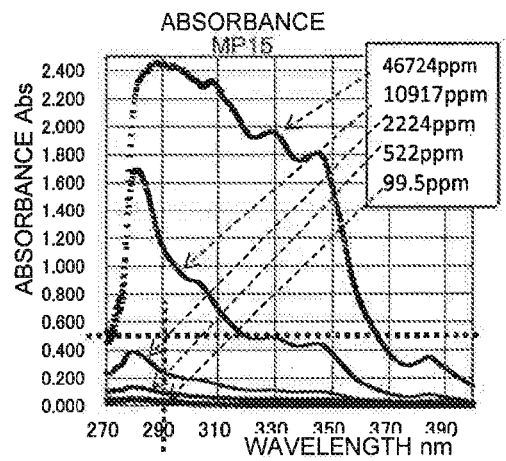
(c) FIRST CALIBRATION CURVE FOR GROUP 1
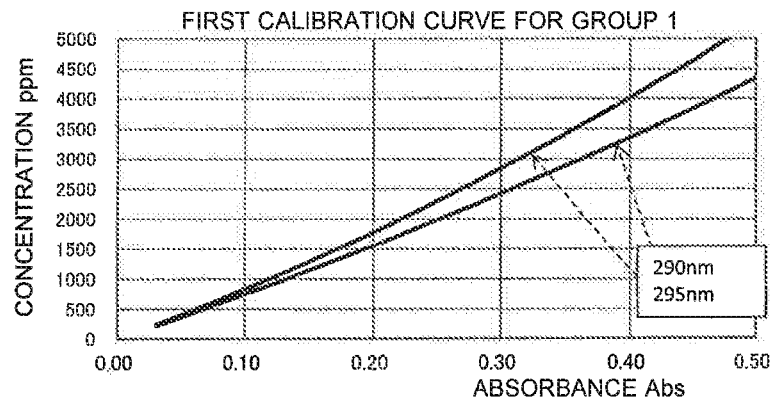
(d) SECOND CALIBRATION CURVE FOR GROUP 1
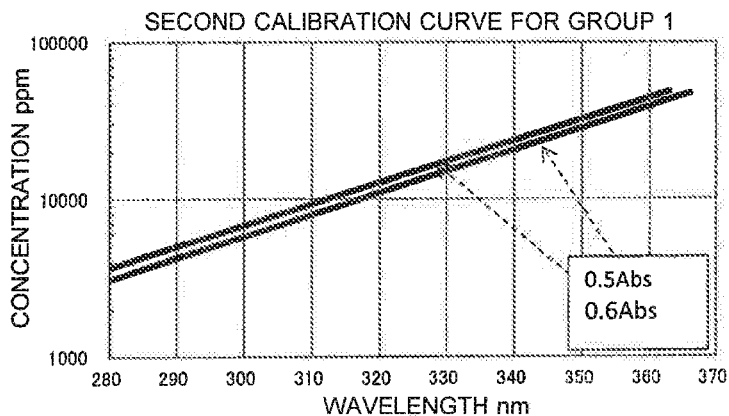

Fig. 5
(a) AMOUNT OF LIGHT TRANSMITTED THROUGH SAMPLE CONTAINING CG8
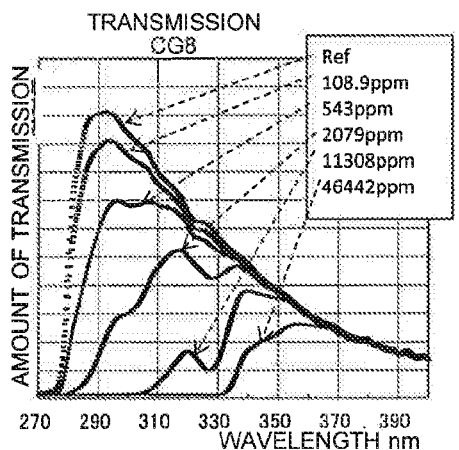
(b) ABSORBANCE OF SAMPLE CONTAINING CG8
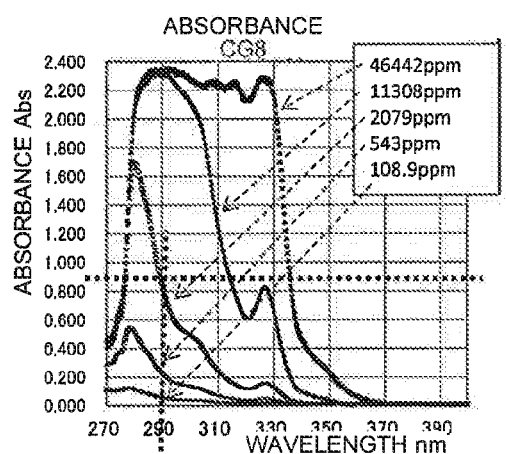
(c) FIRST CALIBRATION CURVE FOR GROUP 2
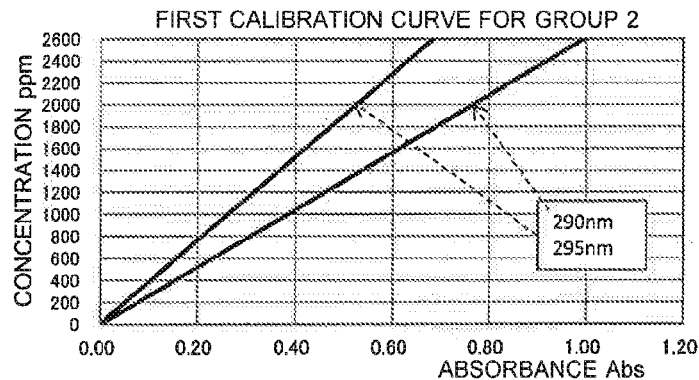
(d) SECOND CALIBRATION CURVE FOR GROUP 2
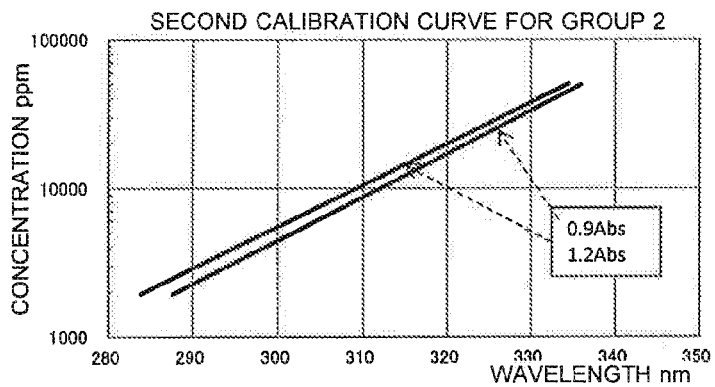

Fig. 6
(a) AMOUNT OF LIGHT TRANSMITTED THROUGH SAMPLE CONTAINING ST25
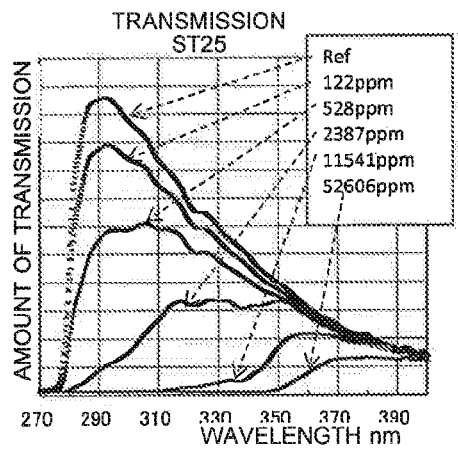
(b) ABSORBANCE OF SAMPLE CONTAINING ST25
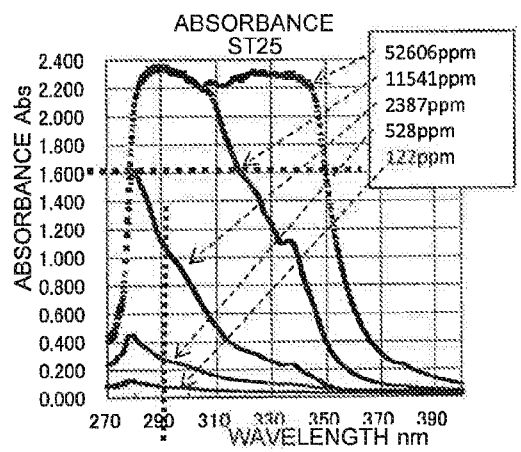
(c) FIRST CALIBRATION CURVE FOR GROUP 3
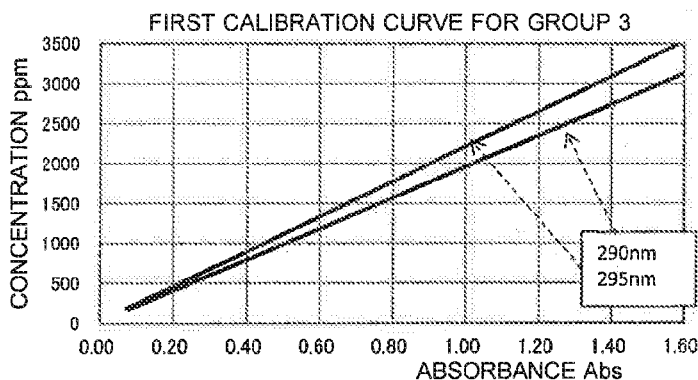
(d) SECOND CALIBRATION CURVE FOR GROUP 3
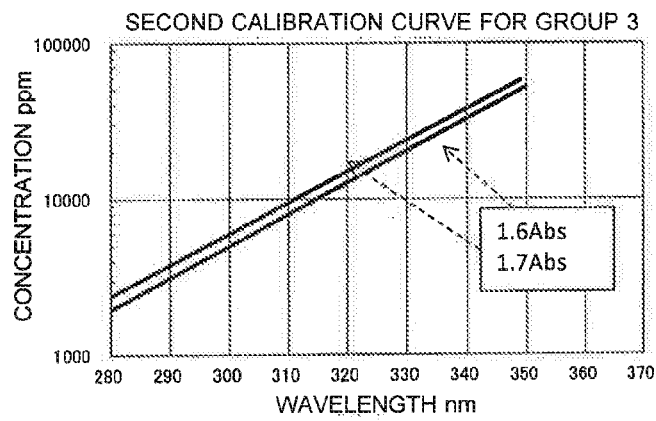

Fig. 7
(a) AMOUNT OF LIGHT TRANSMITTED THROUGH SAMPLE CONTAINING FE205D
(b) ABSORBANCE OF SAMPLE CONTAINING FE205D
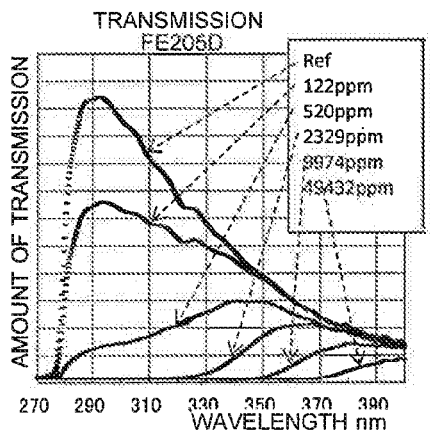
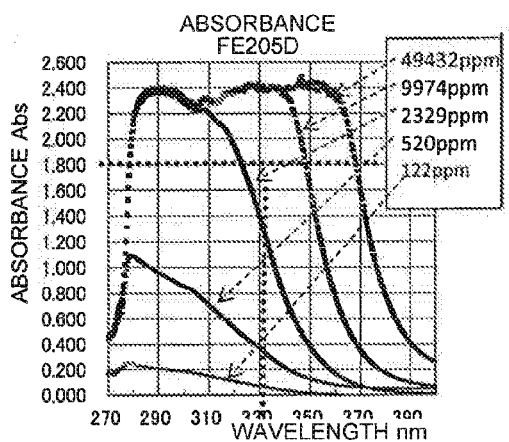
(c) FIRST CALIBRATION CURVE FOR GROUP 4
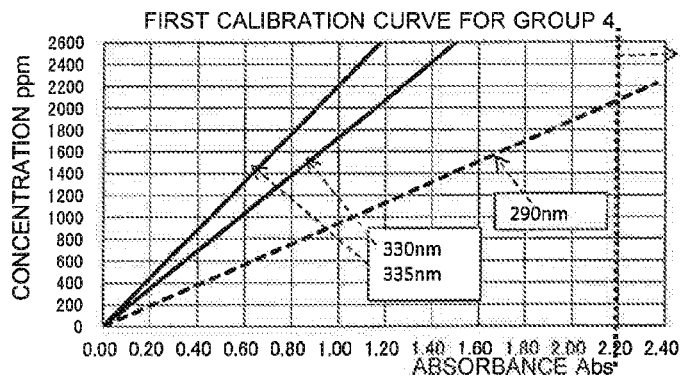
(d) SECOND CALIBRATION CURVE FOR GROUP 4
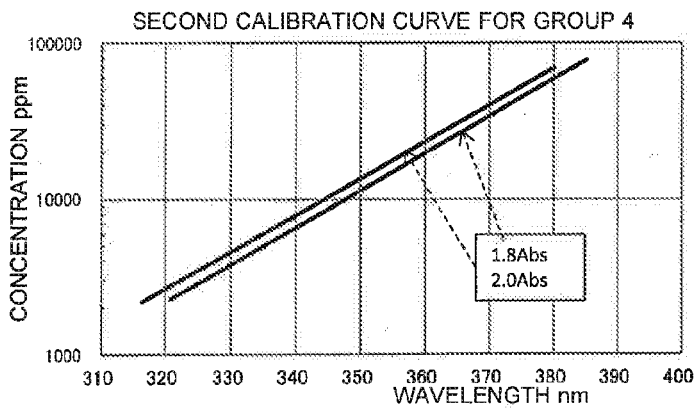

OIL CONCENTRATION MEASUREMENT SYSTEM AND OIL CONCENTRATION MEASUREMENT METHOD

TECHNICAL FIELD

The present invention relates to a system and method for measuring the concentration of oil in a liquid. The present oil concentration measurement system and oil concentration measurement method can be suitably used in industrial cleaning machines which remove organic contaminants (such as cutting oil, press-punching oil, machining oil, grease and flux) from a workpiece, in order to measure the concentration of the oil contained in the cleaning liquid or similar liquid during its use.

BACKGROUND ART

The mainstream of the cleaning liquid used in industrial cleaning machines is hydrocarbon cleaning liquids. Hydrocarbon cleaning liquids have the advantage that they contain neither ozone-depleting substances nor chlorine, and therefore, are not very harmful to the environment or human bodies. Another advantage of the hydrocarbon cleaning liquids exists in that they can be recycled by distillation using the difference in the boiling point from oil components, and furthermore, the clean vapor generated in the recycling process can be utilized for the cleaning and drying of the workpiece (this process is hereinafter called the "vapor-cleaning and drying process"). In the vapor-cleaning and drying process, a workpiece is placed in a cleaning tank for the vapor-cleaning and drying process. After the vapor is introduced into this tank to clean the surface of the workpiece, the tank is rapidly depressurized to suddenly lower the boiling point of the cleaning agent. This causes the bumping and vaporization of the cleaning agent adhered to the surface of the workpiece, whereby the workpiece is dried. In practically used industrial cleaning machines, the vapor-cleaning and drying process for a workpiece is performed as the finishing process after the workpiece has been cleaned with a liquid by being placed in a liquid-cleaning tank holding a hydrocarbon cleaning liquid. A rinsing process using a hydrocarbon cleaning liquid may additionally be performed between the liquid-cleaning process and the vapor-cleaning and drying process.

The cleaning power of a hydrocarbon cleaning liquid depends on the oil concentration in the liquid or its vapor. Furthermore, an increase in the oil concentration of the vapor in the drying process may cause smears to remain. With the repetition of the cleaning of workpieces by the liquid-cleaning process, the oil which is removed as a result of the distillation recycling of the hydrocarbon cleaning liquid used in the liquid-cleaning process accumulates in the distilling tank. This increases the oil concentration in the recycled hydrocarbon cleaning liquid or its vapor. Therefore, it is necessary to regularly boil down the residual liquid in the distilling tank and drain the oil. To "boil down" means to heat the residual liquid in the distilling tank, without the supply of the hydrocarbon cleaning liquid to the distilling tank and that of the vapor from the distilling tank to the cleaning tank for the vapor-cleaning and drying process, so as to vaporize the hydrocarbon cleaning liquid in the residual liquid and condense the residual oil.

The timing of such a boil-down and oil-drainage operation has conventionally been specified for each individual industrial cleaning machine by the manufacturer of the industrial cleaning machine according to the kind of oil to be removed by the machine, use frequency of the oil and other factors. However, in some situations, e.g. immediately after the delivery of the machine, or when the user has changed the kind of oil used for the machining of the workpiece (or other processes), the cleaning or drying performance may become insufficient. In such cases, the oil concentration in the liquid-cleaning tank is measured, and the timing of the boil-down and oil-drainage operation is changed based on the measured result.

Patent Literature 1 discloses a system for determining the concentration of a contaminant dissolved in a cleaning liquid used for the cleaning of a workpiece by measuring an absorbance of the cleaning liquid using ultraviolet radiation having a specific wavelength within a range of 200 to 380 nm, based on a previously created calibration curve which shows the absorbance with respect to the concentration of a known contaminant. This system can be applied to contaminants composed of oil substances, such as cutting oil, working oil, press oil, machine oil, heat treatment oil, grease, and wax. The measurable range of the oil concentration by this system is from 50 to 1000 ppm (1 ppm=1 mg/L). When the concentration exceeds 1000 ppm, the liquid is diluted with a virgin cleaning liquid to a concentration of 1000 ppm or lower levels before the measurement.

Patent Literature 1 also discloses a cleaning system provided with a circulation passage for a rinsing liquid which extends from a second storage tank holding the rinsing liquid and returns to the same second storage tank after passing through a glass cell in an ultraviolet absorptiometer, in order to automatically measure the concentration of the oil remaining in the rinsing liquid used for rinsing a workpiece which has been cleaned with a cleaning liquid. In this cleaning system, the absorbance of the rinsing liquid, i.e. the oil concentration of the rinsing liquid, is continuously measured.

CITATION LIST

Patent Literature

Patent Literature 1: JP 09-061349 A

SUMMARY OF INVENTION

Technical Problem

As noted earlier, the task of setting and changing the timing of the boil-down and oil-drainage operation in the distilling tank is performed based on the measured result of the oil concentration of the hydrocarbon cleaning liquid in the liquid-cleaning tank. Accordingly, if the oil concentration in the liquid-cleaning tank can be automatically and continuously measured, it will be possible to automatically perform the task of setting and changing the aforementioned timing. It will also be possible to modify the conditions of the cleaning process based on the oil concentration in the cleaning liquid so as to perform the cleaning operation under optimized conditions at each point in time. For example, the process can be controlled so that the cleaning is completed in a shorter period of time when the oil concentration of the cleaning liquid is low and the cleaning efficiency is accordingly high, while the cleaning is continued for a longer period of time when the oil concentration of the cleaning liquid is high and the cleaning efficiency is accordingly low. However, in the case of Patent Literature 1, although the oil concentration of the rinsing liquid can be continuously measured, such a continuous measurement is impossible for the cleaning liquid. The reason for this is because the concentration of the oil in the cleaning liquid changes over a much wider range than that of the rinsing liquid, with the highest level reaching approximately 20000 ppm. The system described in Patent Literature 1 cannot directly measure such a high-concentration cleaning liquid whose oil concentration exceeds 1000 ppm; as already noted, the liquid needs to be diluted with a virgin cleaning liquid to a concentration of 1000 ppm or lower levels before the measurement. Since the necessity of the diluting operation changes in this manner depending on the concentration, it is difficult to continuously measure the oil concentration of the cleaning liquid in the system of Patent Literature 1.

If the concentration of the oil in the residual liquid in the distilling tank can be automatically measured, it will be possible to more directly determine the timing of the boil-down and oil-drainage operation. However, the concentration of the oil in the residual liquid in the distilling tank can reach as high as 50000 ppm. Accordingly, for the system of Patent Literature 1, an automatic measurement of the oil concentration in the distilling tank is even more difficult than in the case of measuring the oil concentration of the hydrocarbon cleaning liquid.

The problem to be solved by the present invention is to provide an oil concentration measurement system and oil concentration measurement method which can measure the concentration of oil over a wide concentration range and is therefore applicable in a continuous measurement of the oil concentration.

Solution to Problem

The oil concentration measurement system according to the present invention developed for solving the previously described problem is a system for measuring the concentration of the oil component in a measurement-target liquid in which an oil component is mixed, where the measurement-target liquid contains, as a principal component, a molecule having no multi-valence bond of carbon atoms, while the oil component contains a molecule having a multi-valence bond of carbon atoms, the system including:

a) an absorbance measurement means for measuring an absorbance spectrum for the measurement-target liquid within a predetermined waveband located between 270 and 400 nm where an absorption of light is observed;

b) an oil concentration determining means for low concentrations for determining a concentration value of the oil component based on the absorbance at a predetermined wavelength within the predetermined waveband as well as based on a first calibration curve showing the relationship between the concentration of the oil component and the absorbance at the predetermined wavelength;

c) an oil concentration determining means for high concentrations for determining a concentration value of the oil component based on a wavelength at which the absorbance has a predetermined absorbance value in the absorbance spectrum within the predetermined waveband as well as based on a second calibration curve showing the relationship between the concentration of the oil component and the wavelength at which the absorbance has the predetermined absorbance value; and d) an oil concentration determination method selection means for selecting, based on a predetermined criterion, either the oil concentration determining means for low concentrations or the oil concentration determining means for high concentrations as the means for determining the concentration value of the oil component.

With most kinds of oil components, if the absorbance of ultraviolet radiation is measured, an absorption due to the multi-valence (doubly or triply charged) bond of the carbons in the molecule is observed at a wavelength within the waveband of 270-400 nm. Accordingly, the concentration of the oil component can be determined by measuring the absorbance of the measurement-target liquid within a predetermined waveband located between 270 and 400 nm. Therefore, if the measurement-target liquid is a hydrocarbon cleaning liquid, glycol ether cleaning liquid, water, or similar liquid whose principal component is a molecule having no multi-valence bond of carbon atoms, and if an oil component having a multi-valence bond of carbon atoms is mixed in this measurement-target liquid, the concentration of the oil component can be measured without being affected by the original components of the measurement-target liquid because no multi-valence bond is present in the molecule of the hydrocarbon, glycol ether or water. The predetermined waveband only needs to include a portion or the entirety of the wavelength range of 270-400 nm. That is to say, wavelengths outside the range of 270-400 nm may additionally be included in the predetermined waveband, or a portion of the wavelength range of 270-400 nm may be excluded from it. The "known kind of oil component" does not mean that the composition of the oil component needs to be known; knowledge of the manufacturer and model number of the oil component is sufficient.

The oil concentration determining means for low concentrations performs the process of determining the oil concentration based on a measured value of the absorbance at a predetermined wavelength in a similar manner to the process performed by the conventional oil concentration measurement system. However, if the oil concentration of the measurement-target liquid is high, the amount of transmitted light at that predetermined wavelength may become too low (i.e. the absorbance may become too high), making it impossible to accurately perform the measurement. If the measured value of the amount of transmitted light is inaccurate, it is impossible to obtain an accurate absorbance, so that the oil concentration cannot be accurately determined.

Therefore, the oil concentration measurement system according to the present invention includes, in addition to the oil concentration determining means for low concentrations, the oil concentration determining means for high concentrations for determining the oil concentration of the measurement-target liquid based on the wavelength at which the calculated absorbance has the predetermined absorbance value as well as based on the second calibration curve showing the relationship between the concentration of the oil component and the wavelength at the predetermined absorbance value. The oil concentration determining means for high concentrations can determine the concentration in the case where the oil concentration of the measurement-target liquid is high, based on the predetermined absorbance value which is accurately obtained, without using a high absorbance value which is inaccurate due to the influence of the decrease in the amount of transmitted light.

However, if the oil concentration of the measurement-target liquid is low, the measured absorbance may not reach the predetermined absorbance value. Therefore, the oil concentration measurement system according to the present invention is provided with two means for determining the oil concentration, i.e. the oil concentration determining means for low concentrations and the oil concentration determining means for high concentrations. Which of the two means should be used for determining the oil concentration is decided by the oil concentration determination method selection means based on a predetermined criterion.

As the predetermined criterion, the absorbance at the predetermined wavelength can be used. In this case, the oil concentration determination method selection means selects the oil concentration determination means for low concentrations if the absorbance is not higher than a predetermined value (namely, predetermined absorbance value; or lower than the predetermined value), while it selects the oil concentration determination means for high concentrations if the absorbance is not lower than the predetermined value (or higher than the predetermined value).

In the case where the measurement of the oil concentration is sequentially performed for a plurality of kinds of measurement-target liquid by switching the passage of the measurement-target liquid, the oil concentration determination method selection means may use, as the predetermined criterion, the identification of the passage which is changed according to the kind of measurement-target liquid to be monitored. For example, consider the case of the previously described industrial cleaning machine in which either the liquid in the rinsing tank or the liquid in the distilling tank is introduced into the absorbance measurement means. In the case of the cleaning liquid in the rinsing tank, the oil concentration rarely exceeds 1000 ppm. Therefore, in practice, no problem occurs even if the measurement is performed using only the oil concentration determination means for low concentrations. In the case of the liquid in the distilling tank, using only the oil concentration determination means for high concentration is practically sufficient for the measurement, since no problem occurs in the distilling tank (i.e. there is no need to perform the boil-down and oil-drainage operation) when the oil concentration is less than 10000 ppm. Thus, the selection between the oil concentration determination means for low concentrations and the oil concentration determination means for high concentrations can be made depending on the kind of measurement-target liquid.

The absorbance is given by the common logarithm of a fraction with the intensity of the transmitted light as the denominator and the intensity of a predetermined reference light as the numerator. As the intensity of the reference light, the intensity of the light transmitted through a sample cell holding the measurement-target liquid free from oil components is used. By using this reference light, the influence of the absorption of light by the clean measurement-target liquid (exclusive of oil components) can be suppressed in the process of creating calibration curves. If the light source is deteriorated or left unused for a long period of time, the intensity of the emitted light may possibly be different from the previously measured value. Accordingly, the intensity of the reference light should preferably be measured regularly or when the use of the system is resumed.

The first and second calibration curves can be previously created using a standard sample which contains a known kind (manufacturer and model number) of oil at a known concentration.

The oil concentration measurement system according to the present invention may be configured so that: a plurality of wavelengths within the predetermined waveband are designated as the predetermined wavelength; and the oil concentration determining means for low concentrations determines, for each of the plurality of predetermined wavelengths, an assumed value of the oil concentration based on the absorbance at the predetermined wavelength measured with the absorbance measurement means as well as based on the first calibration curve created at the predetermined wavelength concerned showing the relationship between the oil concentration and the absorbance, and calculates the oil concentration value from a plurality of assumed concentration values obtained. For example, an average, median or similar value of the assumed concentration values can be used in the calculation of the oil concentration value from the plurality of assumed concentration values. Calculating the oil concentration value from a plurality of assumed concentration values obtained using a plurality of predetermined wavelengths in the previously described manner improves the accuracy of the concentration value. Similarly, the system may also be configured so that: a plurality of absorbance values are designated as the predetermined absorbance value; and the oil concentration determining means for high concentrations determines, for each of the plurality of predetermined absorbance values, an assumed oil concentration value based on the wavelength at which the absorbance measured with the absorbance measurement means has the predetermined absorbance value as well as based on the second calibration curve created at the predetermined absorbance value concerned showing the relationship between the oil concentration and the wavelength at which the absorbance has the predetermined absorbance value, and calculates the oil concentration value from a plurality of assumed concentration values obtained.

An example of the predetermined wavelength used in the oil concentration determining means for low concentrations is the wavelength at which the intensity of the transmitted reference light has the highest value (peak top). The reason for this is as follows: When an increase in the concentration of the oil component to be measured causes only a small increase in the absorbance, and when the concentration of that oil component is low, it is the clean measurement-target liquid (exclusive of the oil component) and the sample cell that dominantly contributes to the spectrum of the amount of light transmitted through the measurement-target liquid. In particular, the spectrum of the amount of transmitted light produced by the material used for the sample cell (e.g. quartz) shows a greater amount of change with an increase in the temperature than the spectrum produced by the oil component or clean measurement-target liquid, and shifts toward the longer-wavelength side with an increase in the temperature. In the case of industrial cleaning liquids, which are used at approximately 40-50° C., it is necessary to take into account the influence of the temperature change during and after their use. Such a change in the amount of transmitted reference light associated with the temperature change occurs more noticeably in the middle of the slope of the peak than in the peak-top area. Accordingly, the error due to the temperature change can be reduced by designating, as the predetermined wavelength, the wavelength at which the amount of transmitted reference light has the peak top. However, if the absorbance at the wavelength which gives the peak top of the reference light considerably increases with an increase in the oil concentration, the contribution of the sample cell to the absorbance is relatively small. In such a case, a different wavelength can be designated as the predetermined wavelength, such as a wavelength at which the absorbance of the oil component has a peak.

If the oil concentration measurement system according to the present invention is used in an industrial cleaning machine which repeatedly performs the cleaning of workpieces that have undergone the same kind of machining process, the kind (manufacturer and model number) of oil, such as the cutting oil or press-punching oil, contained in the measurement-target liquid is usually unchanged. Therefore, only the first and second calibration curves corresponding to that oil component need to be used. On the other hand, there is also the case where the kind of oil component contained in the measurement-target liquid can be changed. In this case, although it is possible to prepare one set of first and second calibration curves for each kind of oil component, it will require an enormous amount of calibration curves to be created for a wide variety of oil. In view of this, the present inventor has measured the absorbance for various kinds of working oil using a plurality of samples with different oil concentrations, and has discovered that the various kinds of working oil can be grouped by their uses, with each group including different kinds of working oil which show a similar relationship between the oil concentration and the absorbance, regardless of the difference in the kind of oil. Specifically, those kinds of working oil can be divided into four groups: (1) cutting oil whose use is limited to objects made of metal softer than iron, such as aluminum; (2) cutting oil which can be used for not only soft objects but also hard metal objects, such as iron or stainless steel; (3) cutting oil which is used when boring a deep hole in a hard metal object, such as stainless steel, as well as press-punching oil which contains a comparatively low amount of additive, such as an anti-seize agent; and (4) press-punching oil which contains a high amount of additive.

Using such a grouping method, the oil concentration measurement system according to the present invention may include:

a storage means for storing a plurality of first calibration curves and second calibration curves according to the use of the oil component;

an input means for allowing users to enter the use; and a calibration curve selection means for selecting, from the first calibration curves and the second calibration curves stored in the storage means, the first calibration curve to be used by the oil concentration determination means for low concentrations and the second calibration curve to be used by the oil concentration determination means for high concentrations, based on the use entered via the input means.

Using the calibration curves grouped in this manner reduces the number of the kinds of first and second calibration curves to be prepared. It also eliminates the necessity for users to obtain information about the manufacturer and model number of the oil mixed in the measurement-target liquid.

The oil concentration measurement system according to the present invention may be configured so that:

a passage through which the measurement-target liquid flows is further provided; and a light-casting means casts continuous light into the measurement-target liquid in the passage, while a transmitted light amount measurement means measures the amount of light transmitted through the measurement-target liquid in the passage. This system can continuously measure the concentration of the oil component in the measurement-target liquid flowing through the passage. This configuration may further include a measurement-target liquid switching means for switching the measurement-target liquid flowing into the passage. For example, if this system is applied in an industrial cleaning machine using a hydrocarbon cleaning liquid, both the oil concentration of the cleaning liquid in the liquid-cleaning tank and that of the residual liquid in the diluting tank by switching the measurement-target liquid between the two kinds of liquid.

The oil concentration measurement method according to the present invention is a method for measuring the concentration of the oil component in a measurement-target liquid in which an oil component is mixed, where the measurement-target liquid contains, as a principal component, a molecule having no multi-valence bond of carbon atoms, while the oil component contains a molecule having a multi-valence bond of carbon atoms, the method including the steps of:

measuring an absorbance spectrum for the measurement-target liquid within a predetermined waveband located between 270 and 400 nm where an absorption of light is observed;

determining the concentration value of the oil component, based on the absorbance at a predetermined wavelength within the predetermined waveband as well as based on a first calibration curve showing the relationship between the concentration of the oil component and the absorbance at the predetermined wavelength, if a predetermined criterion is met; and determining the concentration value of the oil component, based on a wavelength at which the absorbance has a predetermined absorbance value in the absorbance spectrum within the predetermined waveband as well as based on a second calibration curve showing the relationship between the concentration of the oil component and the wavelength at which the absorbance has the predetermined absorbance value, if the predetermined criterion is not met.

The previously described oil concentration measurement method can be modified as follows: Instead of initially measuring the absorbance spectrum within the predetermined waveband, the absorbance at the predetermined wavelength is initially measured (accordingly, at this stage, it is unnecessary to measure the absorbance at wavelengths other than the predetermined wavelength), and if the absorbance meets the predetermined criterion, the concentration value of the oil component is determined based on the absorbance and the first calibration curve, whereas, if the absorbance does not meet the predetermined criterion, the absorbance spectrum within the predetermined waveband other than the predetermined wavelength is measured, and the concentration value of the oil component is determined based on the wavelength at which the absorbance has the predetermined absorbance value in the absorbance spectrum as well as based on the second calibration curve.

Advantageous Effects of the Invention

With the present invention, it is possible to obtain an oil concentration measurement system and oil concentration measurement method which can measure the concentration of oil over a wide concentration range and is therefore applicable in a continuous measurement of the oil concentration.

BRIEF DESCRIPTION OF DRAWINGS

FIG. 4 illustrates graphs showing (a) spectra of the amount of transmitted light and (b) absorbance spectra obtained from samples prepared by mixing working oil "MP15" in hydrocarbon cleaning liquid "NS100", as well as (c) the first calibration curves and (d) second calibration curves created based on absorbance spectra obtained from samples in which a kind of working oil belonging to Group 1 was mixed.

FIG. 5 illustrates graphs showing (a) spectra of the amount of transmitted light and (b) absorbance spectra obtained from samples prepared by mixing working oil "CG8" in hydrocarbon cleaning liquid "NS100", as well as (c) the first calibration curves and (d) second calibration curves created based on absorbance spectra obtained from samples in which a kind of working oil belonging to Group 2 was mixed.

FIG. 6 illustrates graphs showing (a) spectra of the amount of transmitted light and (b) absorbance spectra obtained from samples prepared by mixing working oil "ST25" in hydrocarbon cleaning liquid "NS100", as well as (c) the first calibration curves and (d) second calibration curves created based on absorbance spectra obtained from samples in which a kind of working oil belonging to Group 3 was mixed.

FIG. 7 illustrates graphs showing (a) spectra of the amount of transmitted light and (b) absorbance spectra obtained from samples prepared by mixing working oil "FE205D" in hydrocarbon cleaning liquid "NS100", as well as (c) the first calibration curves and (d) second calibration curves created based on absorbance spectra obtained from samples in which a kind of working oil belonging to Group 4 was mixed.

DESCRIPTION OF EMBODIMENTS

An embodiment of the oil concentration measurement system according to the present invention is hereinafter described using FIGS. 1-8.

Embodiment

Figure 1:
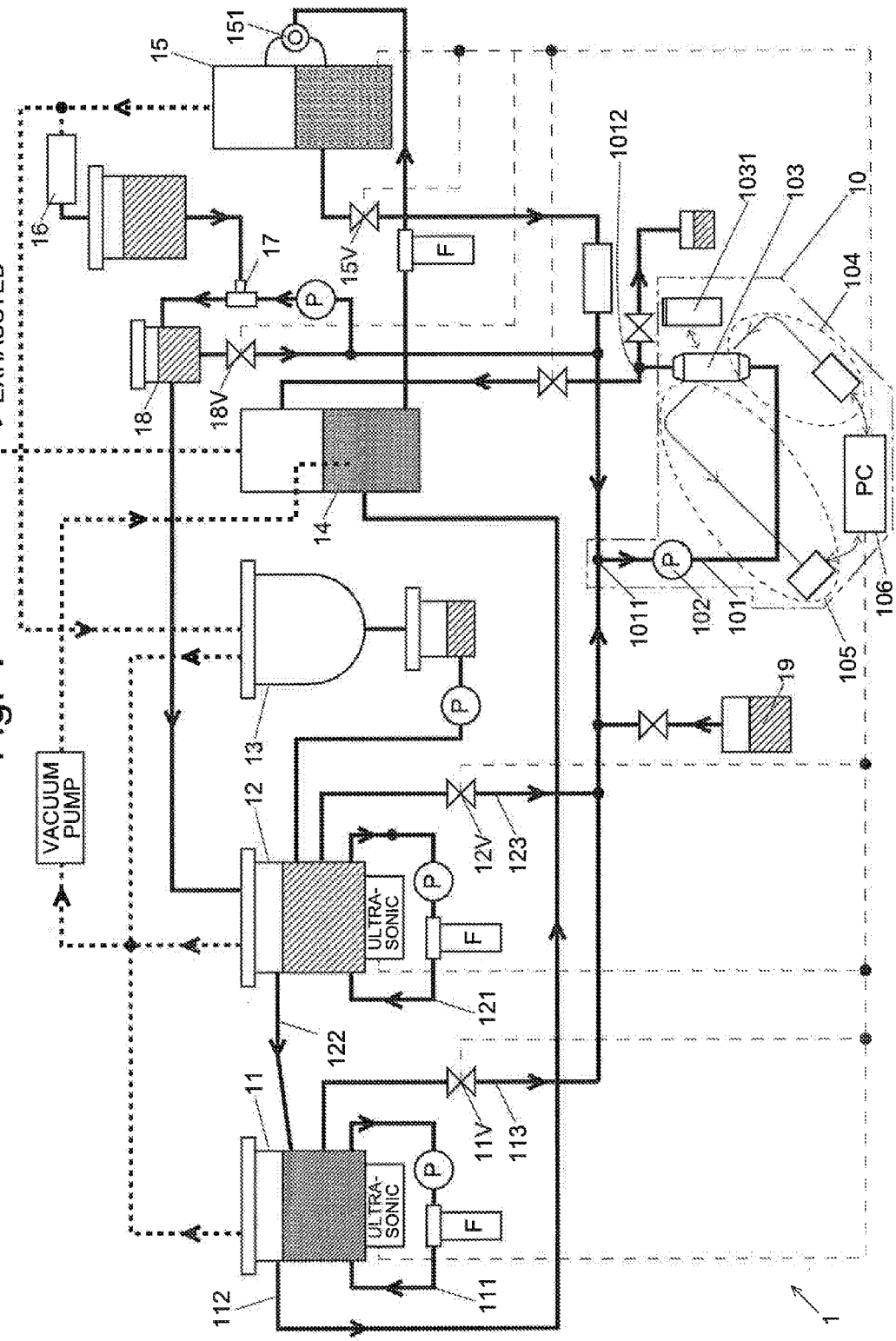
FIG. 1 is a schematic configuration diagram showing an industrial cleaning machine including an embodiment of the oil concentration measurement system according to the present invention as one component.

FIG. 1 shows a schematic configuration of an industrial cleaning machine 1 including the oil concentration measurement system 10 of the present embodiment as one component. The industrial cleaning machine 1 is a system for removing oil adhered to a workpiece and includes, in addition to the oil concentration measurement system 10, a first cleaning tank 11, second cleaning tank 12, vapor-cleaning and drying tank 13, temporary storage tank 14, distilling tank 15, heat exchanger 16, ejector 17, recycled cleaning liquid storage tank 18, and sample-cell-cleaning liquid tank 19. The thick solid lines in FIG. 1 indicate the passages of liquid, the thick broken lines indicate the passages of gas, and the thin broken lines indicate the paths of electric signals.

(1) Overall Configuration and Operation of Industrial Cleaning Machine 1

In advance of the description of the oil concentration measurement system 10 of the present embodiment, the overall configuration of the industrial cleaning machine 1 and its workpiece-cleaning operation is initially described. Each of the first and second cleaning tanks 11 and 12 is provided with an ultrasonic oscillator for giving ultrasonic oscillation to the cleaning liquid stored in the tank. In order to help the generation of the cavitation by ultrasonic waves, the first and second cleaning tanks 11 and 12 are depressurized with a vacuum pump to deaerate the cleaning liquid. After the cleaning liquid is stored in the first and second cleaning tanks 11 and 12, a workpiece is immersed in the cleaning liquid and the ultrasonic oscillation is given, whereby the workpiece is cleaned. Due to a reason (which will be described later), the cleaning liquid in the second cleaning tank 12 has a lower level of oil content than the cleaning liquid in the first cleaning tank 11. Accordingly, the amount of re-adhesion of the oil in the cleaning liquid to the workpiece can be minimized by initially cleaning the workpiece in the first cleaning tank 12 and subsequently cleaning the same workpiece in the second cleaning tank 12.

The second cleaning tank 12 receives an inflow of the recycled cleaning liquid from the recycled cleaning liquid storage tank 18. The recycled cleaning liquid, which is free from oil, is produced by the distilling tank 15 in a manner to be described later. The first and second cleaning tanks 11 and 12 are connected to each other by a second overflow tube 122. The point of connection of the second overflow tube 122 to the second cleaning tank 12 is at a higher level than the point of connection to the first cleaning tank 11. When the level of the cleaning liquid in the second cleaning tank 12 exceeds the point of connection to this tank due to the inflow of the recycled cleaning liquid, a portion of the cleaning liquid in the second cleaning tank 12 automatically moves to the first cleaning tank 11. Accordingly, as noted earlier, the cleaning liquid in the second cleaning tank 12 has a lower level of oil content than the cleaning liquid in the first cleaning tank 11. The first cleaning tank 11 is connected to the temporary storage tank 14 by a first overflow tube 112. When the level of the cleaning liquid in the first cleaning tank 11 exceeds the point of connection of the first overflow tube 112 due to the inflow of the cleaning liquid from the second cleaning tank 12, a portion of the cleaning liquid in the first cleaning tank 11 automatically moves to the temporary storage tank 14 through the first overflow tube 112.

The distilling tank 15 is provided with a float valve 151, which allows the cleaning liquid in the temporary storage tank 14 to flow into the distilling tank 15 when the amount of liquid in the distilling tank 15 falls below a predetermined value due to the distillation. The inner space of the distilling tank 15 is heated by a heater (not shown) as well as depressurized by the ejector 17. By this operation, the cleaning liquid is vaporized, leaving oil components in a liquid state. After being condensed by the heat exchanger 16, the liquid is stored in the recycled cleaning liquid storage tank 18, to be eventually returned to the second cleaning tank 12 in the previously described manner.

The vapor-cleaning and drying tank 13 is a tank for performing the previously described vapor-cleaning and drying process for a workpiece cleaned in the second cleaning tank 12. The vapor used for the vapor-cleaning process and the residual cleaning liquid removed from the surface of the workpiece are returned to the second cleaning tank 12. The gas which results from the depressurization in the first and second cleaning tanks 11 and 12 as well as the vaporization of the cleaning liquid is collected into the used cleaning liquid stored in the temporary storage tank 14. The sample-cell-cleaning liquid tank 19 is a tank for storing a cleaning liquid (which is different from the cleaning liquid that is the target of the oil concentration measurement) used for cleaning the sample cell 103 (which will be described later).

The first cleaning tank 11 has a first circulatory filter system 111 for extracting the cleaning liquid from the tank and returning it to the same tank after passing it through a filter. The second cleaning tank 12 also has a similar, second circulatory filter system 121. These circulatory filter systems are used for removing particles with a diameter of approximately 10 μm or larger and cannot remove oil components.

(2) Configuration of Oil Concentration Measurement System 10 of Present Embodiment Next, the configuration of the oil concentration measurement system 10 in the industrial cleaning machine 1 is described in detail. The oil concentration measurement system 10 includes: a passage 101 connected to the first cleaning tank 11, second cleaning tank 12 and other tanks as will be described later; a liquid-sending pump 102 provided in the passage 101; a sample cell 103 provided on the downstream side of the liquid-sending pump 102 in the passage 101; a reference cell 1031 for a reference measurement; a light-casting section 104; a light-detecting section 105; and a personal computer (PC) 106 which performs calculations and various other processes (which will be described later).

The entrance portion 1011 of the passage 101 is connected to the first cleaning tank 11 via a first relay tube 113 as well as to the second cleaning tank 12 via a second relay tube 123. The first and second relay tubes 113 and 123 are provided with first and second relay on-off valves 11V and 12V, respectively. The entrance portion 1011 of the passage 101 is also connected to the distilling tank 15 and the recycled cleaning liquid storage tank 18. The distilling tank 15 is provided with a distilling tank on-off valve 15V, while the recycled cleaning liquid storage tank 18 is provided with a recycled cleaning liquid storage tank on-off valve 18V.

The exit portion 1012 of the passage 101 is connected to the temporary storage tank 14. Accordingly, the cleaning liquid used for the measurement in the oil concentration measurement system 10 is transferred via the temporary storage tank 14 to the distilling tank 15 and thereby distilled, to be eventually returned to the second cleaning tank 12 in an oil-free state. Alternatively, the cleaning liquid used for the measurement may be directly returned from the exit portion 1012 to the tank in which the liquid was previously stored.

Both the sample cell 103 and the reference cell 1031 are made of quartz which barely absorbs ultraviolet radiation. In a normal measurement, the sample cell 103 is connected in the passage 101, while the reference cell 1031 is connected when the reference is measured. The reference cell 1031 is filled with an oil-free cleaning liquid. The light-casting section 104 is used for casting continuous ultraviolet light into the cleaning liquid in the sample cell 103 (measurement-target liquid). This section includes: a light source for generating the continuous ultraviolet light; and an optical fiber having an entrance end for receiving an input of the continuous ultraviolet light from the light source and an exit end for casting the same light into the cleaning liquid in the sample cell 103. The light-detecting section 105, which corresponds to the aforementioned transmitted light measurement means, detects the intensity of the continuous ultraviolet light transmitted through the cleaning liquid in the sample cell 103 at each wavelength. The light-detecting section 105 includes: a spectrometer for dispersing the transmitted light; an optical fiber having an entrance end for receiving an input of the transmitted light and an exit end for casting the same light onto the spectrometer; and a signal converter for converting the intensity of the transmitted light at each wavelength detected by the spectrometer into digital signals.

Figure 2:
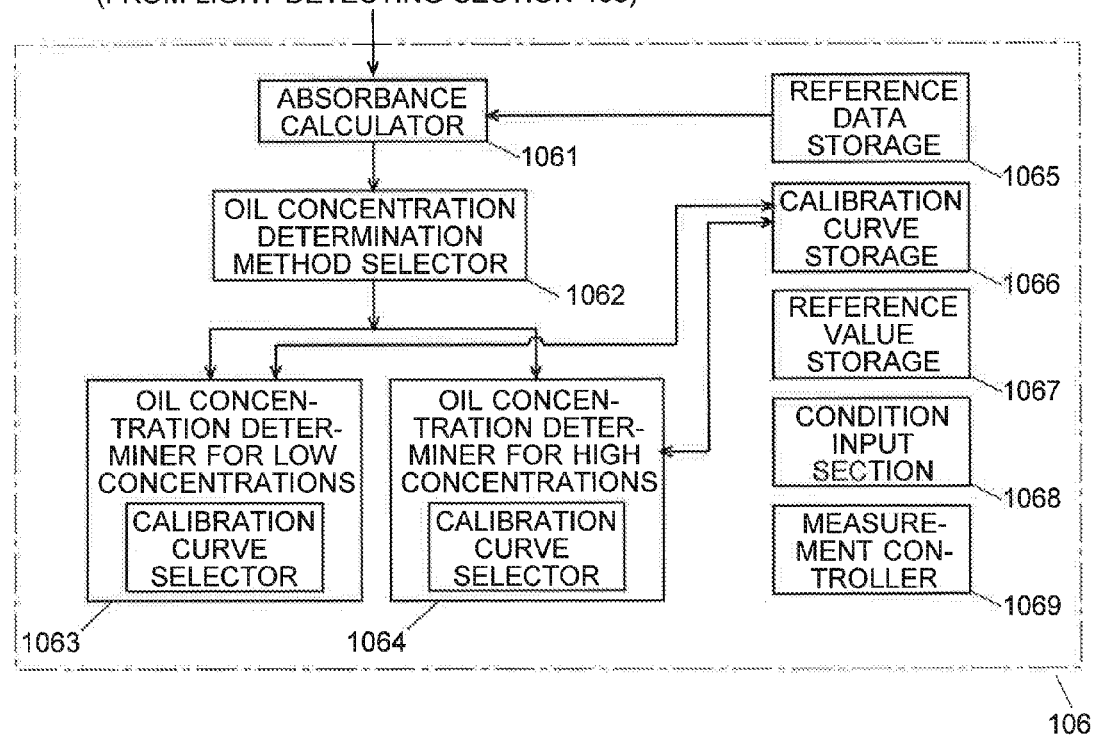
FIG. 2 is a block diagram showing the function of the personal computer (PC) in the oil concentration measurement system of the present embodiment.

As shown in FIG. 2, the PC 106 includes an absorbance calculator 1061, oil concentration determination method selector 1062, oil concentration determiner 1063 for low concentrations, oil concentration determiner 1064 for high concentrations, reference data storage section 1065, calibration curve storage section 1066, reference value (predetermined absorbance value) storage section 1067, condition input section 1068, and measurement controller 1069. Among these elements, the absorbance calculator 1061, oil concentration determiner 1063 for low concentrations, oil concentration determiner 1064 for high concentrations will be described later in detail along with the operation of the oil component measurement system 10 of the present embodiment. The reference data storage section 1065 holds spectrum data of the amount of transmitted light previously measured for an oil-free cleaning agent (reference data). The calibration curve storage section 1066 holds first and second calibration curves created for each group of oil that can be used for processing workpieces based on data previously measured using samples with known oil concentrations. Examples of the first and second calibration curves will be described later. The reference value storage section 1067 holds data of the reference values used by the oil concentration determiner 1064 for high concentrations. The condition input section 1068 allows operators to enter measurement conditions (which will be described later) using input devices, such as a keyboard and mouse. The measurement controller 1069 controls various operations, such as the initiation and discontinuation of the casting of light from the light source in the light-casting section 104 as well as the initiation and discontinuation of the processes in the aforementioned elements.

(3) Operation of Oil Concentration Measurement System 10 of Present Embodiment

Figure 3:
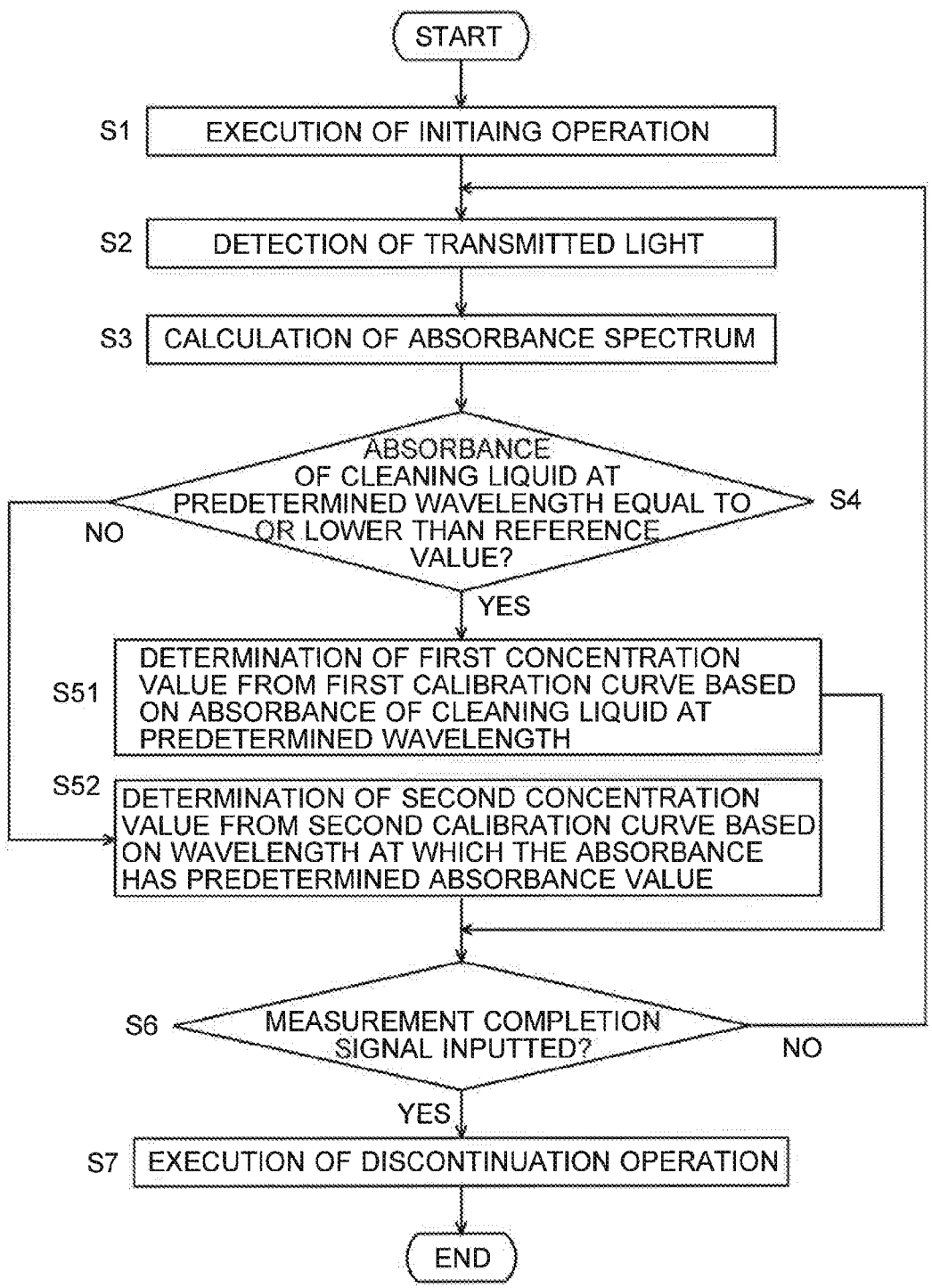
FIG. 3 is a flowchart showing an operation of the oil concentration measurement system of the present embodiment.

An operation of the oil concentration measurement system 10 of the present embodiment is described using the flowchart of FIG. 3. The following description is concerned with the example of performing the measurement for the cleaning liquid stored in the first cleaning tank 11. The measurement for a liquid stored in the second cleaning tank 12, distilling tank 15 or recycled cleaning liquid storage tank 18 is also similarly performed.

Initially, an operator inputs predetermined measurement conditions in the condition input section 1068 and issues a command for initiating the measurement, whereupon the system initiates the measurement. The measurement conditions include information related to the use of the working oil adhered to the workpiece which is cleaned with the cleaning liquid to be monitored. This information is used for identifying the group to which the working oil belongs. For example, the information includes the material of the workpiece (whether the material is a soft material, such as aluminum, or hard material, such as stainless steel) and the working method (cutting work or punch-pressing work). If the manufacturer and model number of the working oil adhered to the workpiece are previously known, the manufacturer and model number may be inputted.

When the measurement is initiated, a predetermined measurement-initiating operation is initially performed (Step S1). For example, the measurement-initiating operation includes the step of opening the first relay on-off valve 11V connected to the first cleaning tank 11 which has been selected in the condition input section 1068. As a result, a portion of the cleaning liquid in the first cleaning tank 11 flows through the first relay tube 113 and the passage 101 into the sample cell 103. This measurement causes no influence on the cleaning process, because the volume of the cleaning liquid in the first cleaning tank 11 is 120 L while the flow rate of the cleaning liquid in the passage 101 is as low as approximately 0.1 L/min, and furthermore, because the cleaning liquid is eventually distilled and returned to the first cleaning tank 11.

The light-casting section 104 casts continuous ultraviolet light into the cleaning liquid in the sample cell 103, while the light-detecting section 105 detects the light transmitted through the cleaning liquid (Step S2). Specifically, the light-detecting section 105 disperses the transmitted light into component wavelengths and converts the intensity of the transmitted light at each wavelength λ, i.e. the spectrum I(λ) of the amount of transmitted light, into digital signals.

The digital signals representing the spectrum I(λ) of the amount of transmitted light I(λ) are sent to the PC 106, and the absorbance spectrum is calculated by the absorbance calculator 1061 (Step S3). Specifically, the absorbance calculator 1061 retrieves, from the reference data storage section 1065, data $I_0(\lambda)$ of the spectrum of the amount of light transmitted through an oil-free cleaning liquid and determines the absorbance A(λ) of the cleaning liquid (i.e. the measurement-target liquid) by the following equation:

$$A(\lambda) = \log_{10}(I_0(\lambda)/I(\lambda))$$

Subsequently, in Step S4, the oil concentration determination method selector 1062 examines the obtained absorbance A(λ) of the cleaning liquid and determines whether or not $A(\lambda_p)$, i.e. the absorbance at predetermined wavelength which is the peak wavelength of the spectrum of the amount of transmitted light previously measured using an oil-free cleaning liquid, is equal to or lower than a predetermined value. The operation proceeds to Step S51 if the absorbance $A(\lambda_p)$ is equal to or lower than the predetermined value, or to Step S52 if the absorbance is higher than the predetermined value.

If the operation has proceeded to Step S51, the oil concentration determiner 1063 for low concentrations determines the oil concentration as follows: The oil concentration determiner 1063 for low concentrations has a calibration curve selector. Initially, this calibration curve selector retrieves, from the calibration curve storage section 1066, the data of the first calibration curve corresponding to the oil-component group which satisfies the conditions entered in the condition input section 1068. The first calibration curve shows the relationship at the predetermined wavelength $\lambda_p$ between the absorbance of the cleaning liquid containing an oil component and the oil concentration. The oil concentration determiner 1063 for low concentrations locates, on the first calibration curve, the concentration value which corresponds to $A(\lambda_p)$, i.e. the absorbance value of the cleaning liquid (i.e. the measurement-target liquid) at the predetermined wavelength $\lambda_p$, and adopts the located concentration value as the concentration value for the measurement-target liquid in question.

If the operation has proceeded to Step S52, the oil concentration determiner 1064 for high concentrations determines the oil concentration as follows: The oil concentration determiner 1064 for high concentrations has a calibration curve selector which is similar to the one provided in the oil concentration determiner 1063 for low concentrations. The calibration curve selector retrieves, from the calibration curve storage section 1066, the data of the second calibration curve corresponding to the oil-component group which satisfies the conditions entered in the condition input section 1068. The second calibration curve shows the relationship between the wavelength at which the absorbance has a predetermined value (predetermined absorbance value) and the oil concentration. The predetermined absorbance value is appropriately determined from the absorbance spectrum taking into account the measurement accuracy. The oil concentration determiner 1064 for high concentrations locates, on the second calibration curve, the concentration value which corresponds to the wavelength value at which the absorbance A(λ) of the cleaning liquid (i.e. the measurement-target liquid) has the predetermined absorbance value, and adopts the located concentration value as the concentration value for the measurement-target liquid in question.

After Step S51 or S52 is completed, in Step S6, the system checks whether or not a measurement discontinuation signal commanding the discontinuation of the measurement operation has been input in the condition input section 1068. If this signal has not been inputted, the operation returns to Step S2. If this signal has been inputted, the measurement is discontinued after the necessary operations are performed, such as closing the first relay on-off valve 11V (Step S7). In this manner, the measurement of the concentration of the sample is repeated until the measurement discontinuation signal is inputted.

As for the first calibration curve, one curve may be prepared for each oil-component group, or a plurality of different curves may be prepared for a plurality of predetermined wavelengths with different values, one curve for one wavelength. In this case, for each of the predetermined wavelengths, the oil concentration determiner 1063 for low concentrations determines one concentration value from the absorbance obtained by the measurement and the first calibration curve corresponding to the predetermined wavelength concerned, and eventually adopts an average of the plurality of obtained concentration values as the concentration value for the measurement-target liquid concerned. Similarly, as for the second calibration curve, one curve may be prepared for each oil-component group, or a plurality of different curves may be prepared for a plurality of different predetermined absorbance values, one curve for one predetermined absorbance value. In this case, for each of the predetermined absorbance values, the oil concentration determiner 1064 for high concentrations determines, from the second calibration curve, one concentration value corresponding to the wavelength value at which the absorbance A(λ) obtained by the measurement has the predetermined absorbance value concerned, and eventually adopts an average of the plurality of obtained concentration values as the concentration value for the measurement-target liquid concerned.

The method described thus far has been concerned with the measurement of the oil concentration of the cleaning liquid in the first cleaning tank 11. The oil concentration of the liquid stored in the second cleaning tank 12, distilling tank 15 or recycled cleaning liquid storage tank 18 can also be similarly measured by operating the valves in the industrial cleaning machine 1 so as to switch the kind of liquid introduced into the passage 101. By continuously measuring the oil concentration in the first and second cleaning tanks 11 and 12, the cleaning quality of the workpiece can be controlled. Specifically, for example, after a workpiece is placed in the first or second cleaning tank 11 or 12, if the oil concentration does not become stabilized but continues to increase even after the passage of a predetermined period of time, the cleaning power will be low, and therefore, the cleaning time in the first or second cleaning tank 11 or 12 should be extended. As another example, if the oil concentration in the recycled liquid in the recycled cleaning liquid storage tank 18 is close to a predetermined upper limit, it is likely that the distilling performance has deteriorated, and therefore, the operation of boiling down the residual liquid in the distilling tank 15 and draining the oil should be performed. Additionally, if the rate of increase in the oil concentration of this recycled liquid exceeds a predetermined value, it is likely that the distilling temperature is too high, and therefore, the temperature should be lowered. The oil concentration of the residual liquid in the distilling tank 15 can also be similarly measured, in which case the thereby obtained oil concentration may be used as a basis for determining the timing of the boil-down and oil-drainage operation.

(4) Example of Absorbance as Well as Data of First and Second Calibration Curves For each of the ten kinds of oil listed in Table 1, a plurality of samples were prepared by mixing the oil at different concentrations in a cleaning liquid of the same composition. Absorbance spectra for those samples were obtained with the oil concentration measurement system of the present embodiment, and the first and second calibration curves were created. The ten kinds of oil are grouped into four categories as shown in Table 1. The first group is the cutting oil whose use is limited to objects made of metal softer than iron, such as aluminum. The second group is the cutting oil which can also be used for hard metal objects, such as iron or stainless steel. The third group is the cutting oil which is used when boring a deep hole in a hard metal object, such as stainless steel, and one which can also be used as press-punching oil. The fourth group is the press-punching oil which contains higher amounts of additive than the third group.

TABLE 1

Working Oil Used in Experiment

| Group No. | Manufacturer and Model Number of Oil | Use of Oil |
| --- | --- | --- |
| 1 | *Idemitsu Kosan, MP15 | Cutting oil for soft metal |
| 2 | *Yushiro Chemical Industry, CG8 Kyowa Oil, GT1S | Cutting oil for hard metal |
| 3 | *Idemitsu Kosan, ST25 Idemitsu Kosan, S50 Nihon Kosakuyu, G718M Nihon Kosakuyu, G7411 | Cutting oil for boring a hole in hard metal Press-punching oil with comparatively low amounts of additive |
| 4 | *Yushiro Chemical Industry, FE205D Yushiro Chemical Industry, FE451 Sugimura Chemical Industrial, S478 | Press-punching oil with higher amounts of additive than Group 3 |

Note:
The asterisks (*) denote the products for which the absorbance and other related data are shown in the graphs of FIGS. 4-7.

FIGS. 4-7 show, for each group, (a) spectra of the amount of transmitted light and (b) absorbance spectra obtained from a sample which contained one representative kind of oil denoted by the asterisk in Table 1. The measurement of the spectrum of the amount of transmitted light (or absorbance) was performed a number of times for each sample with the oil concentration varied from approximately 100 ppm to approximately 50000 ppm. Each of FIGS. 4-7 illustrates spectra obtained at five representative concentrations. Although the graphs (a) and (b) in FIGS. 4-7 show spectra for only four representative kinds of oil, the spectra of the amount of transmitted light and absorbance spectra for the six other kinds of oil were also similarly obtained. With any of the used samples, a peak of absorbance is observed within a wavelength range of 290 to 330 nm.

Subsequently, based on the obtained absorbance spectra, first and second calibration curves were created for each group. The graphs (c) and (d) in each of FIGS. 4-7 respectively show the first and second calibration curves obtained for each group. The calibration curves were created for each group using not only the absorbance spectra obtained from the samples containing the representative kinds of oil shown in the graphs (a) and (b) in FIGS. 4-7 but also those obtained from the samples containing the other kinds of oil. The first calibration curves were created by approximating the relationship between the absorbance value at the predetermined wavelength and the concentration by a function within a concentration range of 5000 ppm or lower for Group 1, 2600 ppm or lower for Groups 2 and 4, as well as 3500 ppm or lower for Group 3. For the creation of the first calibration curves, two predetermined wavelengths were chosen for each group, i.e. 290 inn and 295 nm for Groups 1-3, and 330 nm and 335 nm for Group 4. The reason why the absorbance values at 290 nm and 295 nm were not used for Group 4 was because the absorbance at a concentration of approximately 2000 ppm was high, and the amount of transmitted light was extremely low, so that a considerable amount of error would probably occur. As a general rule, linear functions were used for the approximation, although a quadratic function was used for Group 1, because using a linear function for this group caused a considerable amount of error.

The second calibration curves were created by applying approximate functions to the relationship between the wavelength and the concentration at the predetermined absorbance values specified for each of Groups 1-4. The predetermined absorbance values were specified so that the absorbance of one sample with a concentration of approximately 10000 ppm or higher must always be included, and the absorbance of one sample with a concentration of approximately 2000 ppm should be included whenever possible. Specifically, the following values were used: 0.5 and 0.6 for Group 1, 0.9 and 1.2 for Group 2, 1.6 and 1.7 for Group 3, as well as 1.8 and 2.0 for Group 4. Exponential functions were used for the approximation.

In the previously described manner, the first and second calibration curves can be determined using samples with known concentrations. Using these calibration curves, a measurement for a sample with an unknown concentration can be performed. In the measurement, the following absorbance values are used as the predetermined value of the absorbance $A(\lambda)$ in the previously described Step S4: 4000 ppm for Group 1, 2000 ppm for Groups 2 and 4, as well as 3000 ppm for Group 3.

Using the first and second calibration curves obtained, an experiment for measuring the concentration of oil in a measurement-target liquid by the method according to the present invention has been conducted. In this experiment, the aforementioned NS100 was once again used as the cleaning liquid, with the ten kinds of oil listed in Table 1 added to it. In the experiment, the cleaning liquid and each oil component were weighed and mixed with each other to prepare samples with known concentrations (these concentrations are hereinafter called the "calculated values"), and the calculated and measured values were compared. The measurement was performed using an actual system at room temperature (20° C.). The same measurement, with the samples heated to 48° C., was also conducted. The former measurement was performed for all of the ten kinds of oil, while the latter measurement was performed for the four kinds of oil denoted by the asterisks in Table 1.

Figure 8:
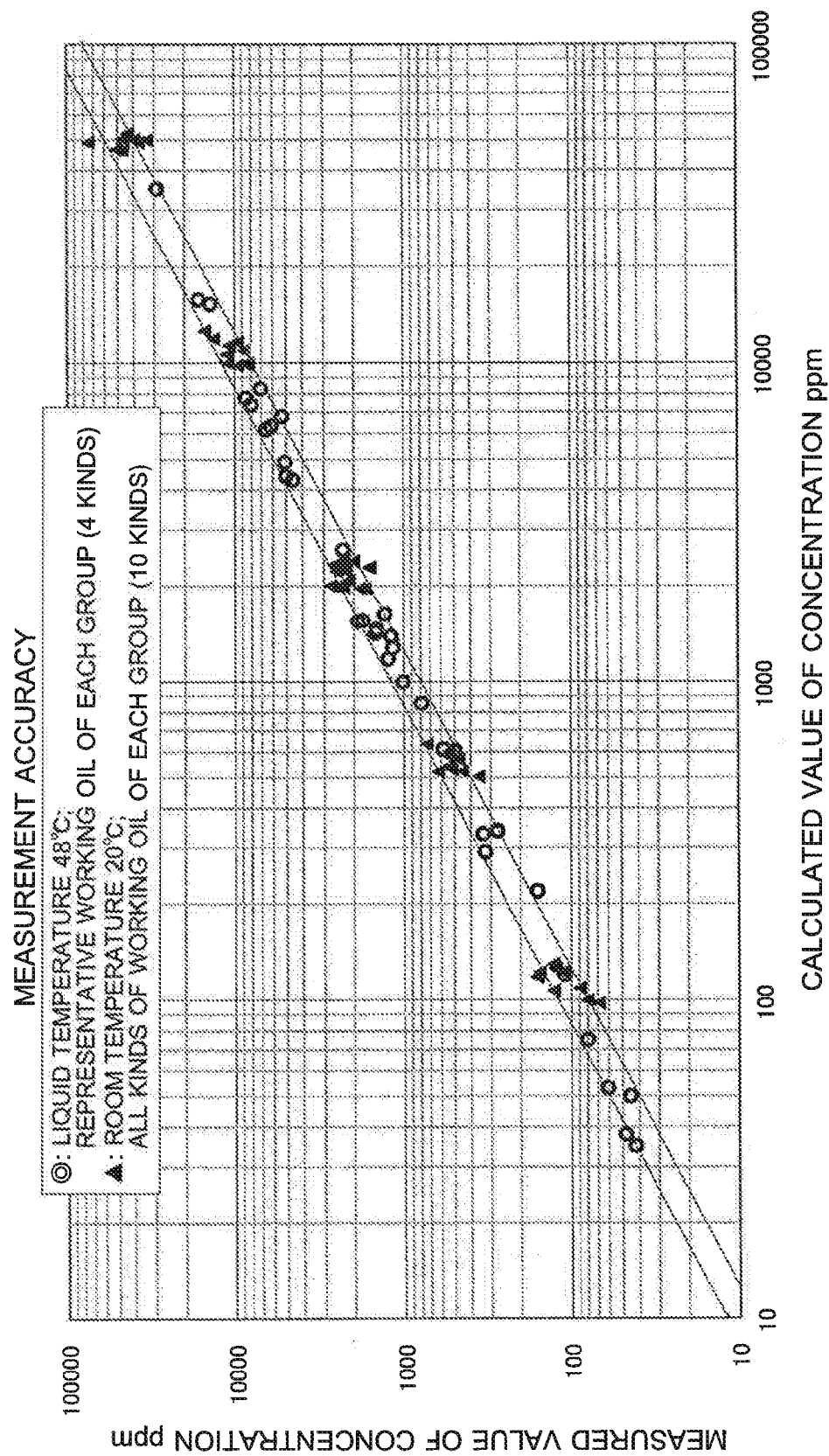
FIG. 8 is a graph with the horizontal axis representing the calculated value of concentration obtained from the volume of the hydrocarbon cleaning liquid and the mass of the oil which were mixed when the sample was prepared, and the vertical axis representing the measured value of the oil concentration obtained by performing a measurement on the sample using the oil concentration measurement system of the present embodiment.

The experimental results were as shown in the graph of FIG. 8. In the graph, the horizontal and vertical axes represent the calculated and experimental values, respectively. Any data point located within the area between the two broken lines in the graph has the experimental value being within a ±20% error range of the calculated value. In FIG. 8, the data obtained for all samples are presented in one graph. As can be seen in this graph, most of the experimental data were within the ±20% error range of the calculated values. An approximately ±20% of accuracy is sufficient for the setting of the cleaning conditions and the distilling conditions for a cleaning liquid in industrial cleaning machines.

REFERENCE SIGNS LIST

1 . . . Industrial Cleaning Machine
101 . . . Passage
1011 . . . Entrance Portion of Passage
1012 . . . Exit Portion of Passage
102 . . . Liquid-Sending Pump
103 . . . Sample Cell
1031 . . . Reference Cell
104 . . . Light-Casting Section
105 . . . Light-Detecting Section
106 . . . Personal Computer (PC)
1061 . . . Absorbance Calculator
1062 . . . Oil Concentration Determination Method Selector
1063 . . . Oil Concentration Determiner for Low Concentrations
1064 . . . Oil Concentration Determiner for High Concentrations
1065 . . . Reference Data Storage Section
1066 . . . Calibration Curve Storage Section
1067 . . . Reference Value Storage Section
1068 . . . Condition Input Section
1069 . . . Measurement Controller
11 . . . First Cleaning Tank
111 . . . First Circulatory Filter System
112 . . . First Overflow Tube
113 . . . First Relay Tube
11V . . . First Relay On-Off Valve
12 . . . Second Cleaning Tank
121 . . . Second Circulatory Filter System
122 . . . Second Overflow Tube
123 . . . Second Relay Tube
12V . . . Second Relay On-Off Valve
13 . . . Vapor-Cleaning and Drying Tank
14 . . . Temporary Storage Tank
15 . . . Distilling Tank
15V . . . Distilling Tank On-Off Valve
16 . . . Heat Exchanger
17 . . . Ejector
18 . . . Recycled Cleaning Liquid Storage Tank
18V . . . Recycled Cleaning Liquid Storage Tank On-Off Valve
19 . . . Sample-Cell-Cleaning Liquid Tank

The invention claimed is:

1. An oil concentration measurement system for measuring a concentration of the oil component in a measurement-target liquid in which an oil component is mixed, where the measurement-target liquid contains, as a principal component, a molecule having no multi-valence bond of carbon atoms, while the oil component contains a molecule having a multi-valence bond of carbon atoms, the system comprising:
 a) an absorbance measurement means for measuring an absorbance spectrum for the measurement-target liquid within a predetermined waveband located between 270 and 400 nm where an absorption of light is observed;
 b) an oil concentration determining means for low concentrations for determining a concentration value of the oil component based on the absorbance at a predetermined wavelength within the predetermined waveband as well as based on a first calibration curve showing a relationship between the concentration of the oil component and the absorbance at the predetermined wavelength;
 c) an oil concentration determining means for high concentrations for determining a concentration value of the oil component based on a wavelength at which the absorbance has a predetermined absorbance value in the absorbance spectrum within the predetermined waveband as well as based on a second calibration curve showing a relationship between the concentration of the oil component and the wavelength at which the absorbance has the predetermined absorbance value; and
 d) an oil concentration determination method selection means for selecting, based on a predetermined criterion, either the oil concentration determining means for low concentrations or the oil concentration determining means for high concentrations as the means for determining the concentration value of the oil component.

2. The oil concentration measurement system according to claim 1, wherein the predetermined criterion is the absorbance at the predetermined wavelength.

3. The oil concentration measurement system according to claim 1, wherein:
 a plurality of wavelengths within the predetermined waveband are designated as the predetermined wavelength; and
 the oil concentration determining means for low concentrations determines, for each of the plurality of predetermined wavelengths, an assumed value of the oil concentration based on the absorbance at the predetermined wavelength measured with the absorbance measurement means as well as based on the first calibration curve created at the predetermined wavelength concerned showing the relationship between the oil concentration and the absorbance, and calculates the oil concentration value from a plurality of assumed concentration values obtained.

4. The oil concentration measurement system according to claim 1, wherein:
 a plurality of absorbance values are designated as the predetermined absorbance value; and
 the oil concentration determining means for high concentrations determines, for each of the plurality of predetermined absorbance values, an assumed oil concentration value based on the wavelength at which the absorbance measured with the absorbance measurement means has the predetermined absorbance value as well as based on the second calibration curve created at the predetermined absorbance value concerned showing the relationship between the oil concentration and the wavelength at which the absorbance has the predetermined absorbance value, and calculates the oil concentration value from a plurality of assumed concentration values obtained.

5. The oil concentration measurement system according to claim 1, wherein the predetermined wavelength is a wavelength at which an intensity of light transmitted through a standard sample free from the oil component is at a highest level.

6. The oil concentration measurement system according to claim 1, further comprising:
- a storage means for storing a plurality of first calibration curves and second calibration curves according to a use of the oil component;
- an input means for allowing users to enter the use; and
- a calibration curve selection means for selecting, from the first calibration curves and the second calibration curves stored in the storage means, the first calibration curve to be used by the oil concentration determination means for low concentrations and the second calibration curve to be used by the oil concentration determination means for high concentrations, based on the use entered via the input means.

7. The oil concentration measurement system according to claim 1, further comprising
- a passage through which the measurement-target liquid flows;
- a light-casting means for casting continuous light into the measurement-target liquid in the passage; and
- a transmitted light amount measurement means for measuring an amount of light transmitted through the measurement-target liquid in the passage.

8. The oil concentration measurement system according to claim 7, further comprising a measurement-target liquid switching means for switching the measurement-target liquid flowing into the passage.

9. An oil concentration measurement method for measuring a concentration of the oil component in a measurement-target liquid in which an oil component is mixed, where the measurement-target liquid contains, as a principal component, a molecule having no multi-valence bond of carbon atoms, while the oil component contains a molecule having a multi-valence bond of carbon atoms, the method comprising steps of:
- measuring an absorbance spectrum for the measurement-target liquid within a predetermined waveband located between 270 and 400 nm where an absorption of light is observed;
- determining a concentration value of the oil component, based on the absorbance at a predetermined wavelength within the predetermined waveband as well as based on a first calibration curve showing a relationship between the concentration of the oil component and the absorbance at the predetermined wavelength, if a predetermined criterion is met; and
- determining a concentration value of the oil component, based on a wavelength at which the absorbance has a predetermined absorbance value in the absorbance spectrum within the predetermined waveband as well as based on a second calibration curve showing a relationship between the concentration of the oil component and the wavelength at which the absorbance has the predetermined absorbance value, if the predetermined criterion is not met.

10. An oil concentration measurement method for measuring a concentration of the oil component in a measurement-target liquid in which an oil component is mixed, where the measurement-target liquid contains, as a principal component, a molecule having no multi-valence bond of carbon atoms, while the oil component contains a molecule having a multi-valence bond of carbon atoms, the method comprising steps of:
- measuring an absorbance for the measurement-target liquid at a predetermined wavelength within a predetermined waveband located between 270 and 400 nm where an absorption of light is observed;
- determining a concentration value of the oil component, based on the absorbance as well as based on a first calibration curve showing a relationship between the concentration of the oil component and the absorbance at the predetermined wavelength, if the absorbance meets a predetermined criterion; and
- measuring an absorbance spectrum for the measurement-target liquid within the predetermined waveband other than the predetermined wavelength, and determining a concentration value of the component based on the wavelength at which the absorbance has a predetermined absorbance value in the absorbance spectrum as well as based on a second calibration curve showing a relationship between the concentration of the oil component and the wavelength at which the absorbance has the predetermined absorbance value, if the absorbance does not meet the predetermined criterion.

* * * * *